United States Patent [19]
Bruemmer et al.

[11] Patent Number: 5,462,541
[45] Date of Patent: * Oct. 31, 1995

[54] POCKET-LIKE DIAPER OR ABSORBENT ARTICLE

[75] Inventors: Mary A. Bruemmer, Appleton; Paulette M. Rosch, Sherwood; John P. Vukos, Neenah; Duane G. Uitenbroek, Little Chute; Georgia L. Zehner, Larsen; Christine A. Rasmussen, Medford, all of Wis.

[73] Assignee: Kimberly-Clark Corporation, Neenah, Wis.

[ * ] Notice: The portion of the term of this patent subsequent to Jan. 5, 2010, has been disclaimed.

[21] Appl. No.: 116,262

[22] Filed: Aug. 18, 1993

Related U.S. Application Data

[63] Continuation-in-part of Ser. No. 882,339, May 13, 1992, abandoned, which is a continuation of Ser. No. 612,168, Nov. 13, 1990, Pat. No. 5,176,672.

[51] Int. Cl.$^6$ ............................................. A61F 13/15
[52] U.S. Cl. ................. 604/391; 604/378; 604/385.1
[58] Field of Search ..................... 604/378, 385.1–391

[56] References Cited

U.S. PATENT DOCUMENTS

| | | | |
|---|---|---|---|
| Re. 33,106 | 11/1989 | Beckestrom | 604/385.2 |
| 2,570,963 | 10/1951 | Mesmer | 128/284 |
| 2,837,095 | 6/1958 | Stevenson | 128/284 |
| 3,073,309 | 1/1963 | Mosier | 128/290 |
| 3,103,930 | 9/1963 | Collett et al. | 128/286 |
| 3,322,122 | 5/1967 | Daniel | 128/284 |
| 3,424,160 | 1/1969 | Koornwinder et al. | 128/286 |
| 3,522,808 | 8/1970 | Worcester | 128/286 |
| 3,532,093 | 10/1970 | Lovret | 128/286 |
| 3,572,342 | 3/1971 | Lindquist et al. | 128/287 |
| 3,626,943 | 12/1971 | Worcester | 128/286 |
| 3,665,920 | 5/1972 | Davis | 128/287 |
| 3,728,744 | 4/1973 | Kimbro, Jr. et al. | 4/113 |
| 3,774,610 | 11/1973 | Eckert et al. | 128/287 |
| 3,779,246 | 12/1973 | Mesek et al. | 128/287 |
| B1 3,860,003 | 4/1989 | Buell | 604/385.2 |
| 3,874,385 | 4/1975 | Gellert | 128/287 |
| 3,888,257 | 6/1975 | Cook et al. | 128/296 |
| 3,890,973 | 6/1975 | Davis et al. | 128/286 |
| 3,920,017 | 11/1975 | Karami | 128/287 |
| 3,927,673 | 12/1975 | Taylor | 128/287 |
| 4,200,102 | 4/1980 | Duhamel et al. | 128/286 |
| 4,230,113 | 10/1980 | Mehta | 128/287 |
| 4,285,342 | 8/1981 | Mesek | 128/287 |
| 4,352,355 | 10/1982 | Mesek et al. | 128/287 |
| 4,388,075 | 6/1983 | Mesek et al. | 604/385 |

(List continued on next page.)

FOREIGN PATENT DOCUMENTS

| | | |
|---|---|---|
| 56789/90 | 12/1990 | Australia . |
| 0157649A2 | 10/1985 | European Pat. Off. . |
| 0336826A1 | 10/1989 | European Pat. Off. . |
| 0343940A2 | 11/1989 | European Pat. Off. . |
| 0359410A1 | 3/1990 | European Pat. Off. . |
| 0396050A2 | 11/1990 | European Pat. Off. . |
| 0403832A1 | 12/1990 | European Pat. Off. . |
| 2561078 | 9/1985 | France . |
| 2573629 | 5/1986 | France . |
| 4016864C1 | 6/1991 | Germany . |
| 63-102704 | 7/1988 | Japan . |
| 63-102705 | 7/1988 | Japan . |
| 33012 | 10/1980 | Taiwan . |
| 2209672A | 5/1989 | United Kingdom . |
| 2265550A | 10/1993 | United Kingdom . |
| WO84/04242 | 11/1984 | WIPO . |

*Primary Examiner*—Randall L. Green
*Assistant Examiner*—Rob Clarke
*Attorney, Agent, or Firm*—Douglas L. Miller; Thomas J. Mielke; John R. Schenian

[57] ABSTRACT

A diaper or absorbent article comprising a topsheet, a backsheet, an absorbent between the topsheet and backsheet, and an elevating device for spacing the topsheet above the absorbent to form a pocket-like shape. The topsheet can have an opening and the absorbent can have a hole therein, both of which receive and isolate waste material from the wearer.

12 Claims, 6 Drawing Sheets

U.S. PATENT DOCUMENTS

| | | | |
|---|---|---|---|
| 4,397,645 | 8/1983 | Buell | 604/380 |
| 4,413,996 | 11/1983 | Taylor | 604/382 |
| 4,425,127 | 1/1984 | Suzuki et al. | 604/366 |
| 4,430,086 | 2/1984 | Repke | 604/385 |
| 4,430,088 | 2/1984 | Karami | 604/385 |
| 4,475,912 | 10/1984 | Coates | 604/385 |
| 4,501,587 | 2/1985 | Enloe | 604/385 |
| 4,610,682 | 9/1986 | Kopp | 604/385 R |
| 4,626,305 | 12/1986 | Suzuki et al. | 156/164 |
| 4,627,846 | 12/1986 | Ternstrom | 604/349 |
| B1 4,636,207 | 11/1989 | Buell | 604/370 |
| 4,639,949 | 2/1987 | Ales et al. | 2/400 |
| 4,642,819 | 2/1987 | Ales et al. | 2/400 |
| 4,646,362 | 3/1987 | Heran et al. | 2/400 |
| 4,661,102 | 4/1987 | Shikata et al. | 604/385 A |
| 4,662,877 | 5/1987 | Williams | 604/385 A |
| 4,675,015 | 6/1987 | Brown | 604/385 R |
| 4,676,785 | 6/1987 | Battista | 604/369 |
| 4,681,581 | 7/1987 | Coates | 604/391 |
| 4,687,477 | 8/1987 | Suzuki et al. | 604/385 A |
| 4,695,278 | 9/1987 | Lawson | 604/385 A |
| 4,704,115 | 11/1987 | Buell | 604/385 A |
| 4,704,116 | 11/1987 | Enloe | 604/385 A |
| 4,728,326 | 3/1988 | Gilles | 604/391 |
| 4,738,677 | 4/1988 | Foreman | 604/385 R |
| 4,743,245 | 5/1988 | Lassen et al. | 604/385 R |
| 4,743,246 | 5/1988 | Lawson | 604/385 A |
| 4,773,906 | 9/1988 | Krushel | 604/391 |
| 4,778,459 | 10/1988 | Fuisz | 604/378 |
| 4,795,451 | 1/1989 | Buckley | 604/385.2 |
| 4,795,452 | 1/1989 | Blaney et al. | 604/385.1 |
| 4,795,454 | 1/1989 | Dragoo | 604/385.2 |
| 4,808,176 | 2/1989 | Kielpikowski | 604/385.2 |
| 4,808,177 | 2/1989 | DesMarais et al. | 604/385.1 |
| 4,822,435 | 4/1989 | Igaue et al. | 156/164 |
| 4,834,737 | 5/1989 | Khan | 604/385.2 |
| 4,834,740 | 5/1989 | Suzuki et al. | 604/385.2 |
| 4,834,742 | 5/1989 | Wilson et al. | 604/389 |
| 4,846,823 | 7/1989 | Enloe | 604/385.2 |
| 4,846,825 | 7/1989 | Enloe | 604/385.1 |
| 4,857,067 | 8/1989 | Wood et al. | 604/389 |
| 4,861,652 | 8/1989 | Lippert et al. | 428/284 |
| 4,880,420 | 11/1989 | Pomparelli | 604/385.1 |
| 4,883,480 | 11/1989 | Huffman et al. | 604/385.1 |
| 4,883,482 | 11/1989 | Gandrez et al. | 604/385.2 |
| 4,892,528 | 1/1990 | Suzuki et al. | 604/385.2 |
| 4,895,568 | 1/1990 | Enloe | 604/385.2 |
| 4,900,318 | 2/1990 | Toth | 604/385.1 |
| 4,904,251 | 2/1990 | Igaue et al. | 604/385.2 |
| 4,909,803 | 3/1990 | Aziz et al. | 604/385.2 |
| 4,916,005 | 4/1990 | Lippert et al. | 428/192 |
| 4,917,696 | 4/1990 | De Jonckheere | 604/385.2 |
| 4,936,840 | 6/1990 | Proxmire | 604/385.2 |
| 4,938,753 | 7/1990 | Van Gompel et al. | 604/385.2 |
| 4,938,754 | 7/1990 | Mesek | 604/385.2 |
| 4,938,757 | 7/1990 | Van Gompel et al. | 604/396 |
| 4,940,464 | 7/1990 | Van Gompel et al. | 604/396 |
| 4,950,262 | 8/1990 | Takagi | 604/385.1 |
| 4,973,326 | 11/1990 | Wood et al. | 604/391 |
| 4,978,570 | 12/1990 | Heyn et al. | 428/231 |
| 4,981,480 | 1/1991 | Gaudet et al. | 604/386 |
| 4,988,344 | 1/1991 | Reising et al. | 604/368 |
| 4,988,346 | 1/1991 | Pfefferkorn | 604/389 |
| 4,988,560 | 1/1991 | Meyer et al. | 428/297 |
| 4,994,054 | 2/1991 | Pigneul et al. | 604/391 |
| 5,019,073 | 5/1991 | Roessler et al. | 604/391 |
| 5,062,840 | 11/1991 | Holt et al. | 604/385.1 |
| 5,171,236 | 12/1992 | Dreier et al. | 604/369 |
| 5,176,672 | 1/1993 | Bruemmer et al. | 604/385.1 |

POCKET-LIKE DIAPER OR ABSORBENT ARTICLE

BACKGROUND OF THE INVENTION

This application is a continuation-in-part of U.S. Ser. No. 07/882,339 filed May 13, 1992 now abandoned, which is a continuation of U.S. Ser. No. 07/612,168 filed Nov. 13, 1990, issued on Jan. 5, 1993, as U.S. Pat. No. 5,176,672.

FIELD OF THE INVENTION

This invention pertains to diapers or other absorbent articles and, more particularly, to a diaper or absorbent article that improves the isolation and containment of waste material from the body.

Currently, disposable diapers or other absorbent articles find widespread use in infant and adult incontinence care and have generally replaced reusable, or washable, cloth absorbent articles. A typical disposable diaper or other absorbent article is a three-layered composite structure comprising a liquid-permeable topsheet, a liquid-impermeable backsheet, an absorbent assembly between the topsheet and backsheet, and a means for fastening the diaper or article to the wearer.

Although current diapers or other absorbent articles have been generally accepted by the public, they still have need of improvement in certain areas, particularly in the area of isolating and containing waste material away from the skin of the wearer. Although current diapers or absorbent articles have been generally satisfactory in preventing leakage of urine outside of the diaper or absorbent article, the waste material contained therein too often is in contact with the skin of the wearer. If this contact between waste material and the skin is prolonged over a period of time, it can cause undesirable effects such as skin dermatitis, skin hydration, or messy clean-ups.

SUMMARY OF THE INVENTION

The present invention provides a diaper or absorbent article that is pocket-like in shape and which receives, isolates, and contains waste material away from the skin of the wearer.

In one form of the present invention, there is provided an absorbent article comprising a backsheet, a topsheet having an opening, an absorbent between the backsheet and topsheet, and an elevating device below the topsheet that spaces the topsheet above the absorbent thereby forming a pocket-like shape for isolating and containing waste material.

In another form of the invention, the opening in the topsheet is generally U-shaped and oriented such that the opening of the "U" faces toward the front edge of the absorbent article.

In yet other forms of the present invention, the absorbent can include a pair of absorbent panels disposed on opposite sides of the absorbent and a pair of elastic members that are attached in a stretched condition to cause the absorbent panels and absorbent to form a pocket-like shape.

BRIEF DESCRIPTION OF THE DRAWINGS

The above-mentioned and other features and objects of this invention, and the manner of obtaining them, will become more apparent, and the invention itself will be better understood, by reference to the following description of the embodiment of the invention taken in conjunction with the accompanying drawings, wherein.

DESCRIPTION OF A PREFERRED EMBODIMENT

The absorbent article of the present invention can be utilized as a baby diaper, adult incontinence garment, and the like. For purposes of the present discussion, the absorbent article will be described in terms of a baby diaper designed to fit a baby weighing between about 12–24 pounds, but it is understood that the features and principles of the present invention apply to other sizes.

Referring to FIGS. 1, 2, 2A, and 8, absorbent article or diaper 10 of the present invention comprises topsheet 12 and backsheet 14 having positioned therebetween absorbent assembly 16. Absorbent assembly 16 includes absorbent structure 18, pledget 20, and hole 22. Masking layer 24 is positioned between absorbent assembly 16 and backsheet 14 so as to underlie hole 22. Cleft block 26 is positioned below or underneath topsheet 12 to elevate a portion of topsheet 12 from absorbent assembly 16 thereby forming a pocket-like structure or shape positioned underneath topsheet 12. Diaper 10 may further comprise elasticized side flaps 28, containment flaps 30, and stretchable ears 32. In order to fasten diaper 10 onto a baby, fasteners 34 are provided on ears 32 and, in this particular embodiment, fasteners 34 comprise hook material 36 on ears 32 and loop material 38 on backsheet 14. Fasteners 34 may also be, or include, other types of mechanical fasteners, adhesive tapes, and the like.

Figure 7:
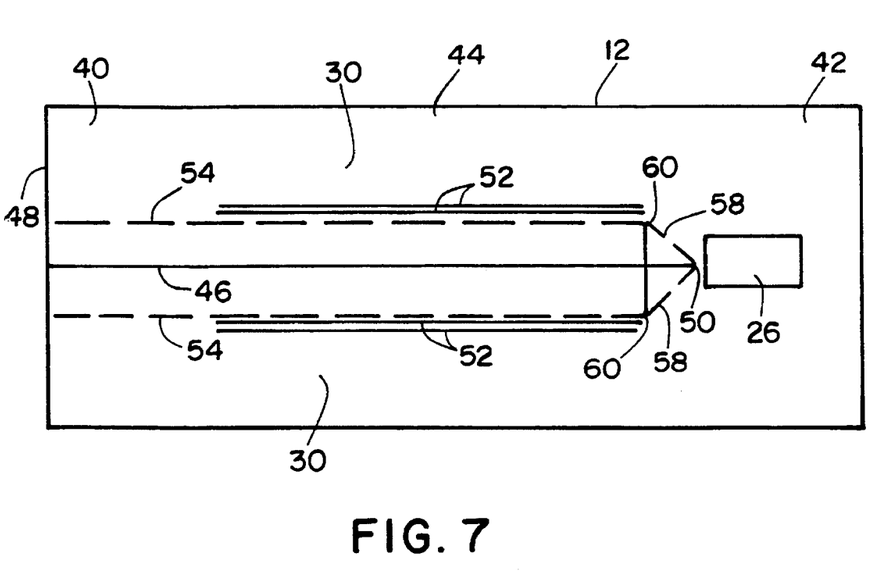
FIG. 7 is a plan view of a liner assembly of the present invention.
Figure 8:
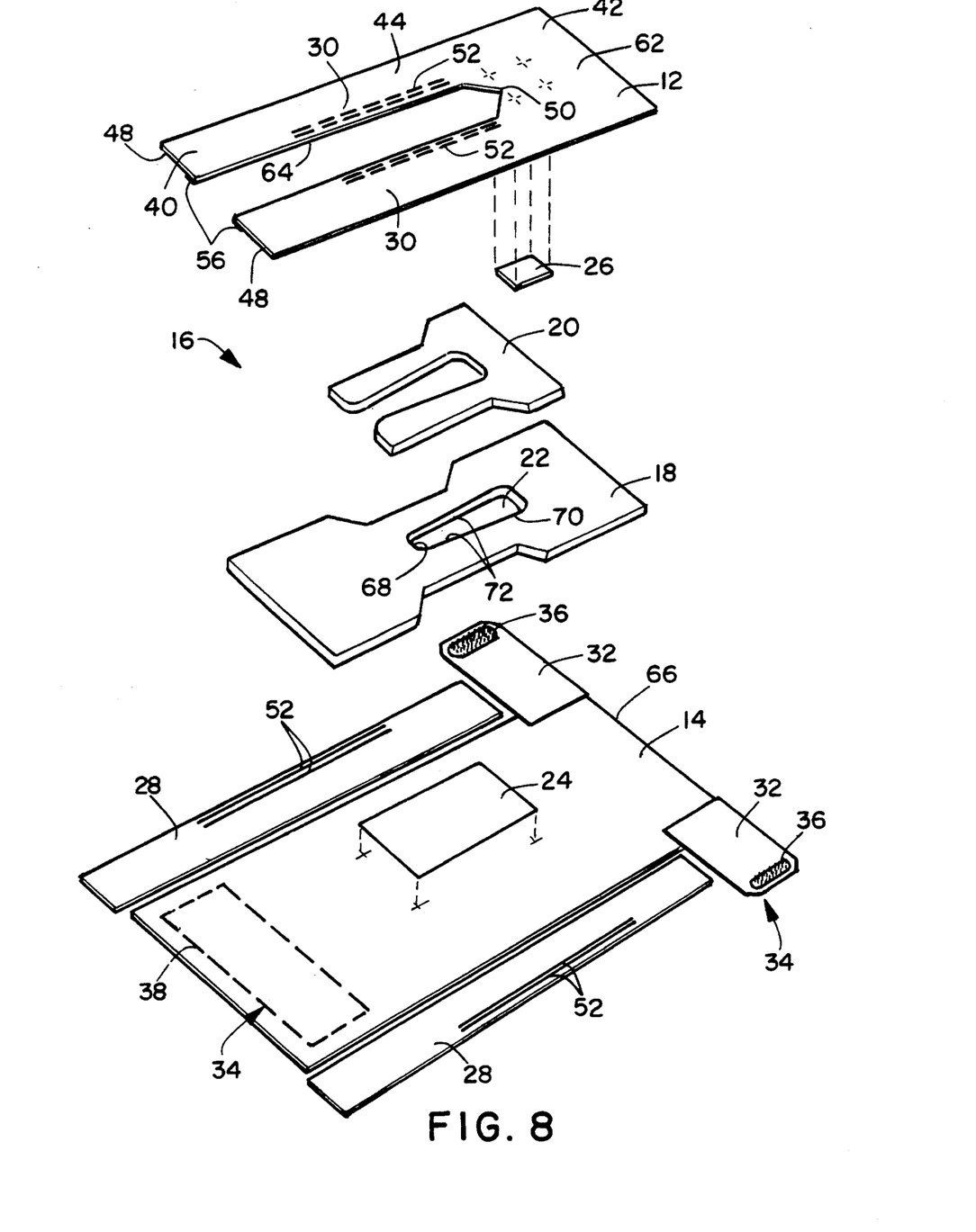
FIG. 8 is an exploded view of the embodiment in FIG. 1.

Referring to FIGS. 7 and 8, topsheet 12 initially is generally rectangular in shape and comprises a front section 40, back section 42, and crotch section 44. In FIG. 8, a finished topsheet 12 has a generally U- or horseshoe-shape in which the elongate portions form containment flaps 30. With reference to FIG. 7, the horseshoe-shape is manufactured by tucking or folding a cut portion of topsheet 12 upon itself starting at longitudinal centerline or cut-line 46, and between front edge 48, to a point in back section 42 identified as apex 50. Prior to cutting and folding topsheet 12 upon itself to form containment flaps 30, an elastic member 52 is applied in a stretched condition in crotch section 44 adjacent to and outboard of, relative to cut-line 46, its respective longitudinal fold-line 54. Elastic members 52 are then covered by topsheet 12 in the cutting and folding step. Each portion of topsheet 12 between cut-line 46 and a longitudinal fold-line 54 is folded against and attached to the remaining portion of topsheet 12 to form folded portions 56 (FIG. 8). During the cutting and folding operation, that part of folded portion 56 near apex 50 is cut and folded along respective fold-lines 58 that converge to apex 50. Fold-lines 58 converge from respective points 60. Alternatively, each portion of topsheet 12, between cut-line 46 and a longitudinal fold-line 54, is cut and removed from topsheet 12, and elastic members 52 are then attached in a stretched condition to flaps 30.

Important to the invention is the spacing between elastic members 52 and the height or width of each containment flap 30 measured in a direction generally perpendicular to cut-line 46. If each elastic member 52 is a single rope, thread, or ribbon of material, the spacing is measured between the mutually facing, innermost edges of the ropes, threads, or ribbons in their stretched condition. The present invention also contemplates each elastic member 52 being a plurality of individual ropes, threads, or ribbons of elastic material. In this latter case, the spacing is measured between the innermost rope, thread, or ribbon of each elastic member 52 in their stretched condition. For example, FIGS. 7 and 8 illustrate each elastic member 52 comprising two ropes or filaments of elastic material placed in a spaced-apart and generally parallel manner near a respective longitudinal fold-line 54. The spacing is then measured between the mutually facing sides of the innermost ropes or filaments of material. Because the elastic members 52 are attached in a stretched condition, at least in a portion of crotch section 44, upon relaxation, they cause containment flaps 30 to move out of the plane of topsheet 12 and to gather.

As mentioned above, the spacing between elastic members 52 and the height or width of containment flaps 30 is important to the invention. For example, if elastic members 52 are spaced too close together and/or containment flaps 30 are too wide or too high, flaps 30 can move into the cleft of the buttocks. This may eventually result in waste material leaking onto the bodyside or top surface 62 (FIG. 8) of topsheet 12 thereby contaminating the baby's skin and making clean-up more difficult and unpleasant. If elastic members 52 are spaced too far apart and/or containment flaps 30 are too short or too narrow, flaps 30 may not seal sufficiently against the body thereby potentially allowing waste material to pass over the sides of containment flaps 30.

Elastic members 52 are preferably spaced apart approximately 4.5 centimeters in the attached, stretched condition. A preferable range of spacing is from about 2 centimeters to about 7 centimeters, and a maximum spacing is from about 1 centimeter to about the total width of diaper 10.

The length of elastic members 52 in the attached, stretched condition is about 19 centimeters in the present embodiment and, depending upon other factors, can be between about 7 centimeters to the entire length of diaper 10. A preferred range is between about 12 centimeters to about 30 centimeters. The length of elastic members 52 can also be defined in terms of the overall length of diaper 10. The length of each elastic member 52 can be between about 30 percent to about 85 percent of the length of diaper 10 and, preferably, about 40 percent to about 60 percent.

In one embodiment, each elastic member 52 is two strands of 470 Decitex Lycra (Decitex being the weight in grams of a single thread which is 10,000 meters long) that are 19 centimeters long when elongated 250 percent. Naturally, any number of strands, including only one, can be used for each elastic member 52 in order to properly and fully elasticize containment flaps 30.

Elastic members 52 are preferably designed to gather containment flaps 30 within the area of crotch section 44 such that the gathered portions of flaps 30 longitudinally terminate between about 2 centimeters to about 10 centimeters from the back and front edges 66 and 67 of diaper 10.

As earlier stated, the height or width of containment flaps 30 is also important to the present invention. A preferred height or width of each containment flap 30 is about 3.5 centimeters. However, depending upon the overall size of diaper 10, each containment flap 30 can have a height or width between about 1 centimeter to about half the total width of diaper 10 and, more preferably, between about 1 centimeter to about 6 centimeters. The height or width of a containment flap 30 is measured between its respective fold-line 54 and the line where the flap is integral with or joined to topsheet 12.

Returning now to FIG. 8, although opening 64 in topsheet 12 is illustrated as having a generally rectangular shape, opening 64 can be of any shape. Topsheet opening 64 passes completely through, or through the entire depth of, topsheet 12 and allows solid fecal matter to move underneath topsheet 12. In this particular embodiment, opening 64 has a preferred area of about 130 square centimeters. Depending upon the size of diaper 10, this area of opening 64 can range between about 30 square centimeters to about 400 square centimeters and, preferably, within the range between about 60 to about 260 square centimeters. Another method of determining or measuring the preferred size of opening 64 is as a percentage of the total area of topsheet 12. For example, in the particular embodiment illustrated, opening 64 comprises about 25 percent of the surface area of topsheet 12. In other embodiments of the present invention, opening 64 can comprise between about 10 percent to about 80 percent of the surface area of topsheet 12.

In forming opening 64 in topsheet 12, it is important that the back of opening 64, such as at apex 50, is positioned so that it is at least about 1 centimeter, and preferably between about 1 centimeter and about 10 centimeters, to the back of and preferably above the level of the wearer's, such as a baby's, anus. Another means of measuring the proper placement of opening 64 is in relation to back edge 66 of diaper 10; and, in this particular embodiment, the back edge of opening 64 is spaced approximately 7 centimeters from back edge 66. Again, depending upon the size of diaper 10, the back edge of opening 64 can be spaced from back edge 66 in a range between about 1 centimeter to about 10 centimeters.

Figure 3:
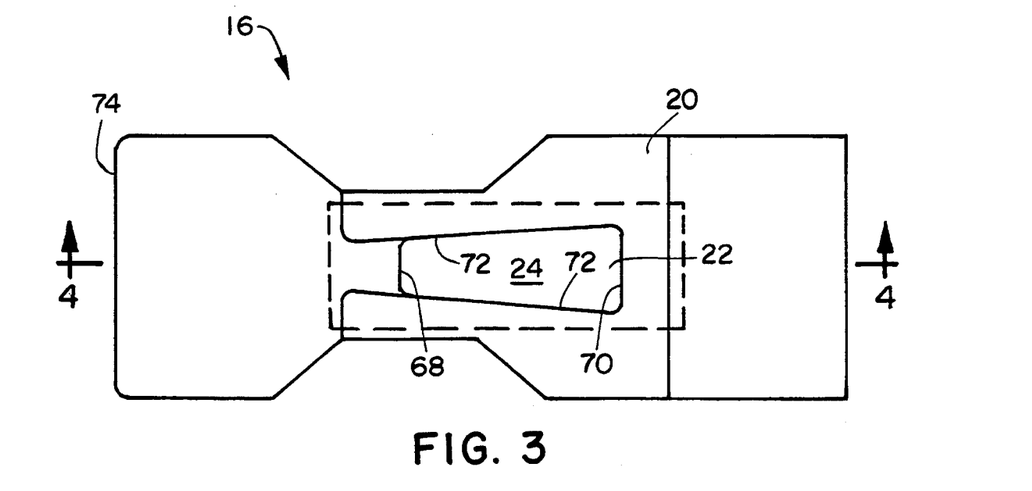
FIG. 3 is a plan view of one absorbent structure of the present invention.
Figure 4:
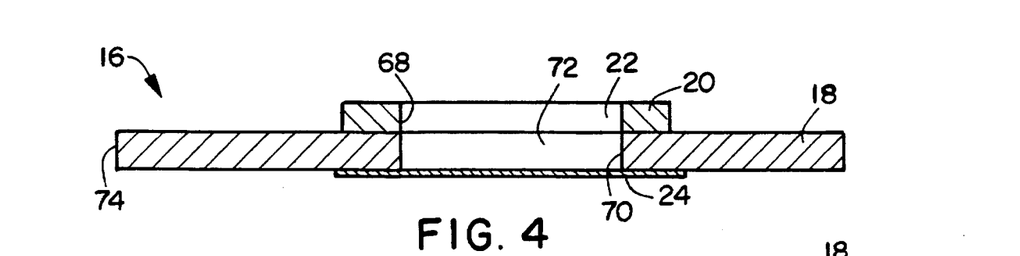
FIG. 4 is a cross-sectional view of the absorbent structure in FIG. 3 taken along line 4—4.

Referring now to FIGS. 3, 4, and 8, absorbent structure 18 is generally hour-glassed shaped, although it may also take on other geometric shapes, such as a generally rectangular or T-shape, and includes hole 22. Hole 22 preferably extends or passes completely through, or through the entire depth of, absorbent article 18. In this particular embodiment, hole 22 is shaped as a trapezoid having front edge 68, back edge 70, and sides 72. Front edge 68, in this embodiment, has a width of about 2.5 centimeters, back edge 70 has a width equal to about 4 centimeters, and sides 72 have a length of about 10 centimeters. Front edge 68 is positioned about 14 centimeters (cm) from front edge 67 of diaper 10 or about 12.5 cm from front edge 74 of absorbent structure 18. Front edge 68 may also be in the range from about 5 cm to about 20 cm from front edge 67 or front edge 74. In order to insure that waste material is received and maintained in hole 22, front edge 68 is preferably also positioned at least about 1 centimeter, and preferably between about 1 centimeter and about 10 centimeters, in front of the wearer's, such as a baby's, anus. Again, the geometric shape and dimensions of hole 22 will depend, among other things, on the overall size of diaper 10. Generally, hole 22 has an area of about 32 $cm^2$, and can have an area within the range of about 5 to about 100 $cm^2$ and, preferably, in a range between about 15 to about 65 $cm^2$.

Hole 22 should also have adequate depth to provide a space or void area to receive and contain feces and, in particular, solid feces. In one embodiment, hole 22 has a depth of about 1 centimeter to receive and contain feces. This depth of hole 22 will naturally vary depending upon the size of diaper 10 and the absorbent materials of which absorbent assembly 16 is made. Consequently, hole 22 can have a minimum depth of about 1 millimeter. There is a preferred relationship between opening 64 in topsheet 12 and hole 22 in absorbent structure 18. The back of opening 64, designated as numeral 50 for example, can be located between about 1 centimeter from diaper back edge 66 to about 1 centimeter from front edge 68 of hole 22. More preferably, the back of opening 64 can be located between about 2 centimeters behind back edge 70 of hole 22 to about 2 centimeters behind front edge 68 of hole 22.

Horseshoe-shaped pledget 20 is positioned on absorbent structure 18 preferably without covering or closing off any portion of hole 22 as illustrated in FIG. 3. Pledget 20 serves several purposes, such as increasing the volume of the void space created by hole 22 and providing additional absorbent material. Superabsorbent material may also be added to pledget 20, or to both pledget 20 and absorbent structure 18, in order to increase absorbency and/or the volume of the void space of hole 22 upon swelling of the superabsorbent material during an insult. As illustrated, horseshoe-shaped pledget 20 has a length of about 12.5 centimeters and a width of about 5 centimeters and partially encircles hole 22. Preferably, the open end of pledget 20 is positioned to face forward or toward the front of diaper 10. However, it can face the back of diaper 10, totally encircle hole 22, or be a series of two or more smaller pledgets of various shapes. Generally, pledget 20 will have a length in the range between about 8 centimeters to the maximum length of absorbent structure 18, a maximum width equal to the width of absorbent structure 18, and a depth between about 1 millimeter to about 3 centimeters.

Pledget 20 and absorbent structure 18, either singly or together, can be enveloped by a layer of tissue or other material to maintain integrity of the absorbent material and to prevent migration of any superabsorbent present therein.

Figure 5:
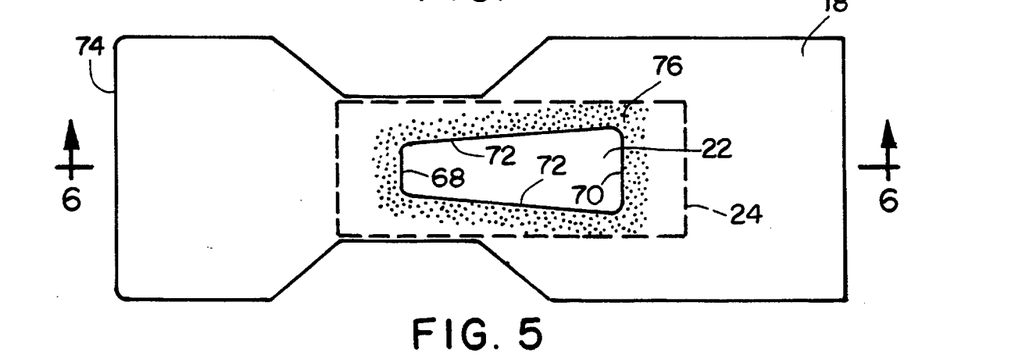
FIG. 5 is a plan view of a second absorbent structure of the present invention.
Figure 6:
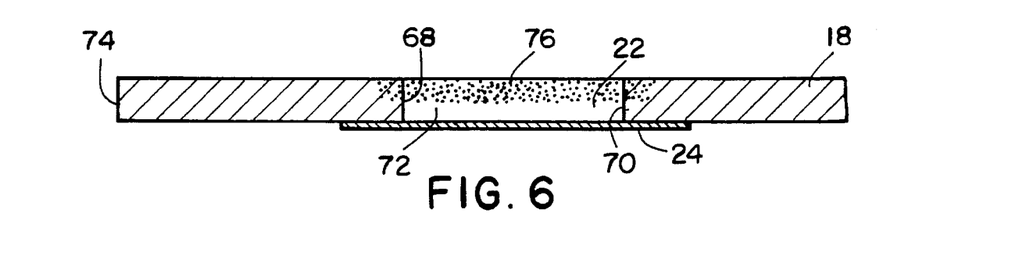
FIG. 6 is a cross-sectional view of the absorbent structure in FIG. 5 taken along line 6—6.

Referring to FIGS. 5 and 6, absorbent structure 18 has an area 76 of zoned superabsorbent material encircling hole 22. Upon a urine insult of zoned area 76, the swelling of area 76 can provide additional space or void volume to receive and contain feces. Zoned area 76 can have any desired shape or density suitable for the particular absorbent structure desired.

Figure 9:
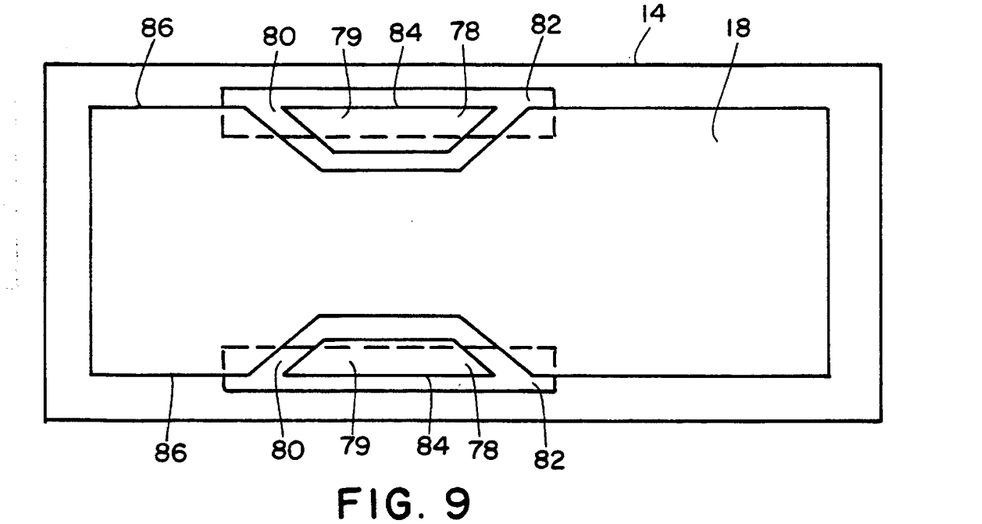
FIG. 9 is a plan view of one assembly of an absorbent structure and a backsheet of the present invention.

Referring to FIG. 9, portions 79 of absorbent structure 18 have been cut away to form leg cut-outs 80 and separate absorbent panels 78. Each panel 78 is spaced from absorbent structure 18, and a stretched elastic member 82 is then positioned between panel 78 and backsheet 14 and attached to one, two, or all of panel 78, absorbent structure 18, and backsheet 14, thereby forming a pocket-like shape. The attachment(s) of the elastic member 82 can be to any portion of panel 78, absorbent structure 18, or backsheet 14, such as the sides or edges. Panel 78 can be trimmed, if desired, so that its outermost edge 84 is aligned with longitudinal edge 86 of absorbent structure 18. Upon relaxing stretched elastic member 82, panel 78 will curl or move upwardly. Panel 78 can be spaced away from leg cut-out 80 between about 1 millimeter to about 2 centimeters and is preferably spaced apart between about 5 millimeters to about 1 centimeter.

Figure 10:
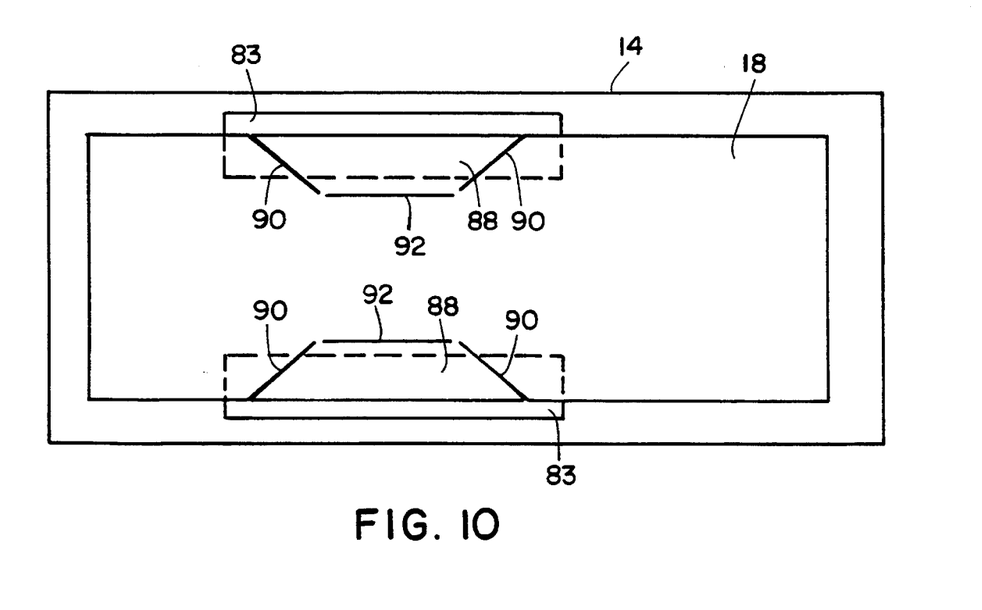
FIG. 10 is a plan view of a second assembly of an absorbent structure and a backsheet of the present invention.

In FIG. 10, integral absorbent panels 88 are formed by cutting absorbent structure 18 along cut-lines 90 and scored along score-line 92. Elastic members 83 are then attached in a stretched condition to one, two, or all of panel 88, absorbent structure 18, and backsheet 14. The attachment(s) of the elastic members 83 can be to any portion of panel 88, absorbent structure 18, or backsheet 14, such as the sides or edges. Upon relaxation of elastic members 83, panels 88 curl or move upwardly.

Referring to FIGS. 1, 2A, 7, and 8, cleft block 26 is an elevating means and is disposed below topsheet 12 and just slightly behind, or to the rear of, opening 64. Cleft block 26 is important to the present invention in that it performs at least two desired functions. One of those functions is to aid in preventing fecal matter and, particularly, solid fecal matter, from moving up the cleft of the baby's buttocks. The second function is to space topsheet 12 above absorbent assembly 16 by elevating at least a portion of topsheet 12 away from absorbent assembly 16 to form a pocket-like void thereby allowing fecal matter and, particularly, solid fecal matter, to move underneath topsheet 12 rather than along its top and against the baby's skin. Cleft block 26 may be between and contact both topsheet 12 and absorbent 18. The pocket-like shape is positioned underneath the topsheet 12.

Cleft block 26 can be made of any suitable material, such as a foam material, cellulosic material, a coform material comprising cellulosic and synthetic fibers, any synthetic or combination of synthetic fibers, absorbent material, thermoplastic material, and the like. Its geometric form is preferably rectangular in shape, but can be any suitable shape that functions as desired.

In this particular embodiment, cleft block 26 is approximately 4 centimeters long, 2 centimeters wide, and about 1 centimeter thick and can be positioned between apex 50 and back edge 66 of diaper 10.

Figure 1:
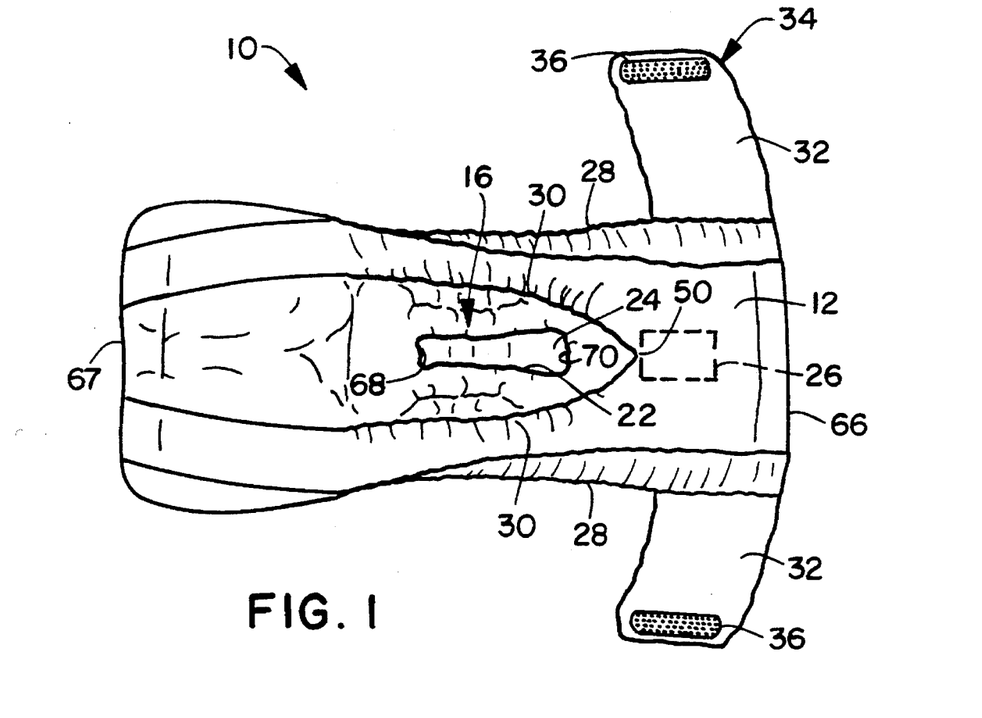
FIG. 1 is a top plan view of one embodiment of the present invention.
Figure 2:
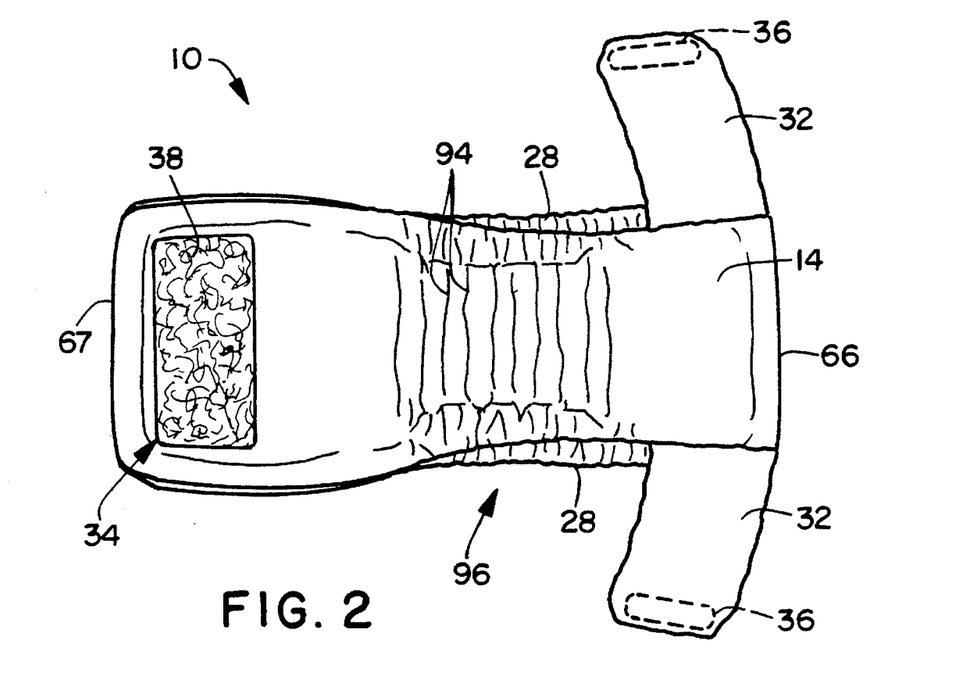
FIG. 2 is a bottom plan view of the embodiment in FIG. 1.
Figure 2A:
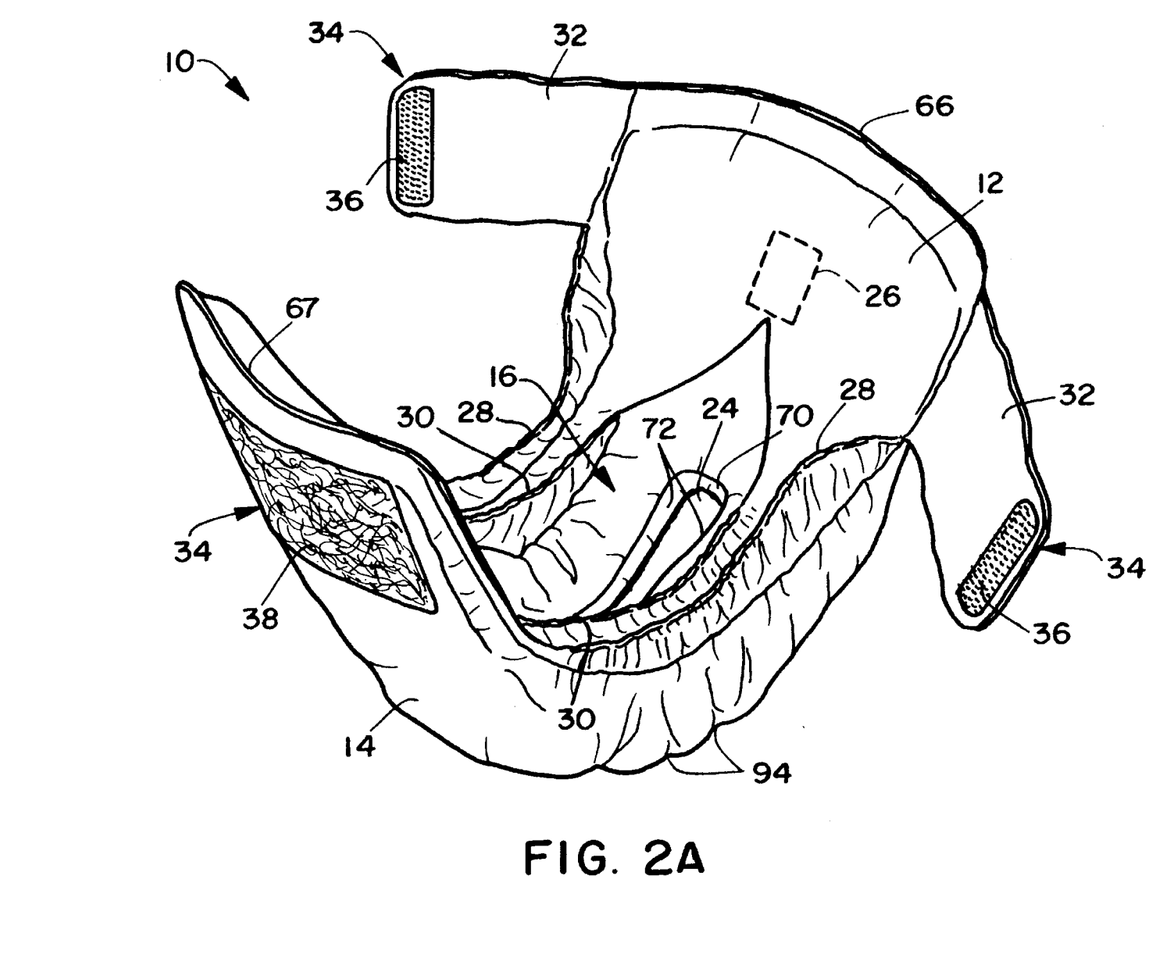
FIG. 2A is a perspective view of the embodiment in FIG. 1.

Referring to FIGS. 1, 2A, and 7, masking layer 24 is at the base of absorbent hole 22 and generally on top of backsheet 14. Masking layer 24 can comprise an absorbent material and/or superabsorbent material thereby acting as an additional absorbent layer. Another function of masking layer 24 is to prevent feces from possibly showing through backsheet 14. Preferably, masking layer 24 comprises two layers; a top layer made from the same material as the material enveloping pledget 20 and absorbent structure 18, thereby providing aesthetic continuity within absorbent assembly 16, and a bottom layer of a thermoplastic film having a thickness of at least about 0.5 mil.

Referring now to FIGS. 2 and 2A, backsheet 14 is preferably longer than topsheet 12 or absorbent assembly 16 and has a plurality of pleats 94 formed therein to permit expansion of backsheet 14. Pleats 94 can be formed in any suitable manner and can have any suitable dimensions. Pleats 94 are preferably formed in crotch area 96 of backsheet 14. In this particular embodiment, backsheet 14, when extended, is about 40 centimeters long and topsheet 12 is about 35 centimeters long.

Topsheet 12 can be a liquid-permeable, hydrophilic or hydrophobic material, such as a spunbonded web composed of synthetic polymer filaments, a spunlace web, a spunbond-meltblown web, a meltblown web, or a bonded-carded web composed of synthetic polymer fibers. Suitable synthetic polymers include polyethylene, polypropylene, polyester, and nylon. In one embodiment, the polymer filaments have a denier within the range of about 1.5 to about 7 denier and, preferably, within the range of about 1.2 to about 6.0 denier. The filaments are arranged to form a layer having a basis weight within the range of about 10 to about 35 grams per square meter (gsm) and, preferably, a basis weight of about 20 gsm. Topsheet 12 can have a bulk thickness within the range of about 0.0140 to about 0.0432 centimeters and, preferably, within the range of about 0.0180 to about 0.305 centimeters. The bulk thickness is measured under a restraining pressure of about 0.014 psi.

Topsheet 12 also can be a Kraton meltblown/polypropylene spunbond stretch-bonded laminate which has been made wettable by addition of surfactants; a polyurethane spunbond material such as that manufactured by Kanebo Synthetic Fibers Company, Osaka, Japan, and made wettable by addition of surfactants; an elastomeric film made from elastomers such as rubber, latex rubber, polyurethane, Kraton, and the like, which has been perforated to allow fluid passage; a polyurethane foam which has been perforated to allow fluid passage; and a nonwoven which has been gathered through the use of elastic or other means, for example, heat-shrinkable fibers, to produce an elastically stretchable material.

Containment flaps 30 are generally of the same material as topsheet 12, although the present invention contemplates that portions of containment flaps 30 could be of a different material than the remaining portion of topsheet 12. For example, all or portions of flaps 30 can be vapor and liquid permeable, vapor permeable and liquid impermeable, or vapor and liquid impermeable.

Backsheet 14, in one embodiment, can be a liquid-impermeable material and, preferably, a polyethylene film having a thickness of about 1.0 mil, although thicknesses above 0.50 mil are acceptable. Backsheet 14 can also be made of other materials that are suitably liquid impermeable or treated to be so. Examples are meltblown or film material made of polypropylene or polyolefin copolymers, such as ethylene vinyl acetate, ethylene methyl acrylate, ethylene ethyl acrylate, polyvinyl chloride, and the like. Other materials include a single spunbonded layer of the above types of material, two layers of spunbonded and meltblown materials, or three layers of material of spunbonded-meltblown-spunbonded material, each of which is suitably treated or coated to be liquid impermeable. The same materials may also be provided in laminate form. The spunbonded materials provide an added feature of a cloth-like texture to backsheet 14. Backsheet 14 may also be made of the material that is not only liquid impermeable, but also vapor permeable. Backsheet 14 can also be made of materials which are easily expandable to provide more room for fecal evacuation and management. For example, backsheet 14 can be made of a microcreped material or materials or can be made of an elastic material or materials.

Side flaps 28 are preferably made of a liquid-impermeable material that is vapor permeable for increased air circulation in the crotch region but may be made, if desired, from a liquid- and vapor-impermeable material or a liquid- and vapor-permeable material. Side flaps 28 can also have selected portions that are liquid permeable with the remaining portions being liquid impermeable. Side flaps 28 can be formed from extensions of backsheet 14 and/or lateral sides of topsheet 12 or can be separate structural elements attached to backsheet 14 and/or topsheet 12. Side flaps 28 can be made of any materials of which topsheet 12 or backsheet 14 can be made.

Side flaps 28 are elasticized and can be made so in the same way that elastic members 52 elasticize containment flaps 30. Elastic members 52 can be any suitable elastic material, such as natural rubber, synthetic rubber, or thermoplastic elastomeric polymers, and can be single or multiple threads, filaments, or ribbons thereof. Optionally, these materials can be heat shrinkable or heat elasticizable. Preferably, each elastic member 52 comprises two or more strands or filaments of about 470–620 Decitex Lycra and, at 90 percent of ultimate elongation, provide a tension between about 25 grams to about 150 grams. The material permits containment flaps 30 and side flaps 28 to retract from about 30 percent to about 80 percent of their elongated length. More preferably, the material has about 50 grams force after one minute hold-time at 90 percent ultimate elongation and the ability to retract to at least about 45 percent to about 50 percent of the original length.

Side flaps 28 preferably comprise two layers of 0.8 ounces per square yard (osy) spunbonded polypropylene and can be liquid permeable, liquid impermeable, or liquid impermeable-vapor permeable. For example, side flaps 28 can comprise at least one layer of a nonwoven, such as a spunbonded, bonded-carded web, or spun-laced material comprised of polymers, such as polypropylene, polyethylene, polyester, or nylon. The material is preferably nonwettable (hydrophobic) in nature. This 0.8 osy side flap comprises a layer of 0.8 osy spunbonded polypropylene which is disposed over an elastic member, such as elastic member 52, to produce a two-layer flap.

Absorbent structure 18 and pledget 20 can be made of any suitable absorbent materials, can comprise the same absorbent materials, or comprise a different combination of absorbent materials. The absorbent materials can include cellulosic fibers, synthetic fibers, absorbent gelling materials in the form of particles, fibers, layers and the like, and various mixtures or blends thereof. Suitable absorbent gelling materials, i.e., superabsorbent materials, can be inorganic materials such as silica gels, or organic compounds such as cross-linked polymers. Some examples of superabsorbent or absorbent gelling material polymers include polyacrylamides, polyvinyl alcohol, polyacrylates, and the like. Other acceptable polymers include acrylonitrile grafted starch, acrylic acid grafted starch, modified carboxy methyl cellulose, and the like.

Absorbent structure 18 and pledget 20 can be individually wrapped in a tissue material, or wrapped as one assembly with a tissue material, in order to maintain fiber integrity and to prevent migration of the superabsorbent material.

Masking layer 24 can also be made of any suitable material, such as those materials of which topsheet 12, backsheet 14, and absorbent assembly 16 are made, or mixtures thereof.

While this invention has been described as having preferred embodiments, it will be understood that it is capable of further modifications. This application is, therefore, intended to cover any variations, uses, or adaptations of the invention following the general principles thereof, and including such departures from the present disclosure as come within known or customary practice in the art to which this invention pertains and fall within the limits of the appended claims.

What is claimed is:

1. An absorbent article, comprising:

a backsheet, a topsheet having an opening therein, wherein said opening allows solid fecal matter to move underneath said topsheet, an absorbent having a hole therein and being between said backsheet and said topsheet, wherein said hole extends through said absorbent, an elevating means below said topsheet for elevating at least a portion of said topsheet away from said absorbent, thereby forming a shape effective to allow solid fecal matter to move underneath said topsheet, wherein said shape is positioned underneath said topsheet, and a masking layer being positioned between said backsheet and said absorbent, wherein said masking layer comprises a first layer of absorbent material and a second layer of liquid-impermeable material.

2. The article of claim 1 wherein said first layer further comprises a superabsorbent material.

3. An absorbent article, comprising:

a backsheet, a topsheet having an opening therein, wherein said opening allows solid fecal matter to move underneath said topsheet.

an absorbent having a hole therein and being between said backsheet and said topsheet, wherein said hole extends through said absorbent, an elevating means below said topsheet for elevating at least a portion of said topsheet away from said absorbent, thereby forming a shape effective to allow solid focal matter to move underneath said topsheet, wherein said shape is positioned underneath said topsheet, a masking layer being positioned between said backsheet and said absorbent, and an absorbent pledget member disposed adjacent said hole.

4. The article of claim 3 wherein said pledget member partially encircles said hole.

5. The article of claim 3 wherein said pledget member totally encircles said hole.

6. The article of claim 3, 4, or 5 wherein said pledget member includes a superabsorbent material.

7. An absorbent article, comprising:

a backsheet, a topsheet having an opening therein, wherein said opening allows solid fecal matter to move underneath said topsheet, an absorbent having a hole therein and being between said backsheet and said topsheet, wherein said hole extends through said absorbent, wherein said absorbent comprises generally opposite panels, an elevating means below said topsheet for elevating at least a portion of said topsheet away from said absorbent, thereby forming a shape effective to allow solid focal matter to move underneath said topsheet, wherein said shape is positioned underneath said topsheet, a masking layer being positioned between said backsheet and said absorbent, and a pair of elastic members attached with at least one of said backsheet, said absorbent, and respective ones of said absorbent panels.

8. The article of claim 7 wherein each said elastic member is attached in a stretched condition to its respective said absorbent panel and said backsheet.

9. The article of claim 7 wherein each said elastic member is attached in a stretched condition to its respective said absorbent panel and said absorbent.

10. The article of claim 7 wherein each said elastic member is attached in a stretched condition to said absorbent and said backsheet.

11. The article of claim 7 wherein each said elastic member is attached in a stretched condition to said absorbent, said backsheet, and its respective said absorbent panel.

12. A method of making an absorbent article, comprising the steps of:

providing a backsheet and a topsheet having an opening therein, wherein said opening allows solid focal matter to move underneath said topsheet, positioning an absorbent with a hole, wherein said hole extends through said absorbent, between the backsheet and the topsheet, providing a pledget member adjacent the hole in the absorbent, elevating at least a portion of the topsheet from the absorbent, and providing a masking layer between the absorbent and the backsheet.

\* \* \* \* \*